United States Patent
Yoon

(10) Patent No.: US 9,120,839 B2
(45) Date of Patent: Sep. 1, 2015

(54) URSOLIC ACID DERIVATIVE AND METHOD FOR PREPARING SAME

(71) Applicant: Nexoligo Co., Ltd., Seoul (KR)

(72) Inventor: Yeo-Hong Yoon, Seoul (KR)

(73) Assignee: NEXOLIGO CO., LTD., Seoul (KR)

( * ) Notice: Subject to any disclaimer, the term of this patent is extended or adjusted under 35 U.S.C. 154(b) by 0 days.

(21) Appl. No.: 14/420,978

(22) PCT Filed: Aug. 2, 2013

(86) PCT No.: PCT/KR2013/007003
§ 371 (c)(1),
(2) Date: Feb. 11, 2015

(87) PCT Pub. No.: WO2014/027777
PCT Pub. Date: Feb. 20, 2014

(65) Prior Publication Data
US 2015/0218206 A1    Aug. 6, 2015

(30) Foreign Application Priority Data

Aug. 14, 2012 (KR) .................. 10-2012-0089026
Aug. 2, 2013 (KR) .................. 10-2013-0091893

(51) Int. Cl.
| | | |
|---|---|---|
| C07D 317/30 | (2006.01) | |
| C07D 305/14 | (2006.01) | |
| C07J 63/00 | (2006.01) | |
| A61K 47/48 | (2006.01) | |
| C07J 75/00 | (2006.01) | |
| A61K 31/56 | (2006.01) | |

(52) U.S. Cl.
CPC ............ *C07J 63/008* (2013.01); *A61K 31/56* (2013.01); *A61K 47/48023* (2013.01); *A61K 47/48061* (2013.01); *C07J 75/00* (2013.01)

(58) Field of Classification Search
CPC ........................ C07D 317/30; C07D 305/14
See application file for complete search history.

(56) References Cited

U.S. PATENT DOCUMENTS

| | | |
|---|---|---|
| 3,909,089 A | 9/1975 | Springer |
| 4,530,934 A | 7/1985 | Clavenna |
| 2009/0075946 A1 | 3/2009 | Ochiai et al. |
| 2011/0019038 A1 | 1/2011 | Okuno |
| 2011/0190388 A1 | 8/2011 | Lin et al. |

FOREIGN PATENT DOCUMENTS

| | | |
|---|---|---|
| CN | 101792477 | 8/2010 |
| CN | 101928322 | 12/2010 |
| CN | 102558279 | 7/2012 |
| EP | 1889850 | 2/2008 |

OTHER PUBLICATIONS

Yunlong Li, Da Xing, Qun Chen, and Wei R. Chen, "Enhancement of chemotherapeutic agent-induced apoptosis by inhibition of NF-jB using ursolic acid", International Journal of Cancer, Jul. 2010, vol. 127, Issue 2, p. 462-473.

Steven D. Kunkel, Manish Suneja, Scott M. Ebert, Kale S. Bongers, Daniel K. Fox, Sharon E. Malmberg, M. Fariborz Alipour, Richard K. Shields, and Christopher M. Adams, "mRNA Expression Signatures of Human Skeletal Muscle Atrophy Identify a Natural Compound that Increases Muscle Mass", Cell Metabolism Article, Jun. 2011, vol. 13, Issue 6, 8, p. 627-638.

Xu Wang, Kenichi Ikejima, Kazuyoshi Kon, Kumiko Arai, Tomonori Aoyama, Kyoko Okumura, Wataru Abe, Nobuhiro Sato, and Sumio Watanabe, "Ursolic acid ameliorates hepatic fibrosis in the rat by specific induction of apoptosis in hepatic stellate cells", Journal of Hepatololgy, Dec. Aug. 2011, vol. 55, p. 379-387.

Yaoyao Jia, Muhammad Javidul Hague Bhuiyan, Hee-jin Jun, Ji Hae Lee, Minh Hien Hoang, Hak-Ju Lee, Nahyun Kim, Dongho Lee, Kwang Yeon Hwang, Bang Yeon Hwang, Dal-Woong Choi, Sung-Joon Lee, "Ursolic acid is a PPAR-a agonist that regulates hepatic lipid metabolism", Bioorganic and Medicinal chemistry Letters, Dec. 2011, vol. 21, p. 5876-5880.

Dong won Jeong, Hye Suk Lee et al., "Dose-linear pharmacokinetics of Oleanolic acid afterintravenous and oral administration in rats.", Biopharmaceutics and Drug Disposision, Mar. 2007, vol. 28, Issue 2, p. 51-57.

Kalani, K. et al., "Pharmacophore, QSAR, and ADME based semisynthesis and in vitro evaluation of ursolic acid analogs for anticancer activity", Journal of molecular modeling, Jul. 2012, vol. 18, pp. 3389-3413.

Zhong, Y. et al., "Synthesis, stability and pharmacological evaluation of a novel codrug consisting of lamivudine and ursolic acid", European journal of pharmaceutical sciences, Nov. 2011, vol. 45, pp. 110-150.

*Primary Examiner* — Sun Jae Yoo
(74) *Attorney, Agent, or Firm* — Lex IP Meister, PLLC

(57) ABSTRACT

The present invention relates to a novel ursolic acid derivative as an ursolic acid prodrug form, and to a method for preparing same, wherein the novel ursolic acid derivative as an ursolic acid prodrug can have excellent pharmacokinetic characteristics such as stability and oral absorptivity and exhibit excellent pharmaceutical activities by being converted into an ursolic acid in vivo. The ursolic acid derivative can be in an ester form in which C28 carboxylic acid in the ursolic acid is combined with a prodrug of a certain pharmaceutical compound.

8 Claims, No Drawings

URSOLIC ACID DERIVATIVE AND METHOD FOR PREPARING SAME

TECHNICAL FIELD

The present invention relates to a novel ursolic acid derivative and a method for preparing the same. More specifically, the present invention relates to a novel ursolic acid derivative as an ursolic acid prodrug form which can have excellent pharmacokinetic characteristics such as stability and oral absorptivity, and exhibit excellent pharmaceutical activities by being converted into an ursolic acid in vivo, and a method for preparing the same.

BACKGROUND ART

An ursolic acid is a pentacyclic triterpene acid compound which is possible to be extracted from natural products such as rosemary leaves, and the like. The ursolic acid is regarded as a natural product-derived compound contained in various plants such as apples, particularly, bark, lavender, basil, rosemary, olegano, thyme, and the like.

The ursolic acid may be represented by Chemical Formula 1 below, and may be referred to as a chemical name: 3β-hydroxy-urs-12-en-28-oic acid. The ursolic acid has a molecular weight of about 456.68 and has a general formula of $C_{30}H_{48}O_3$.

Chemical Formula 1

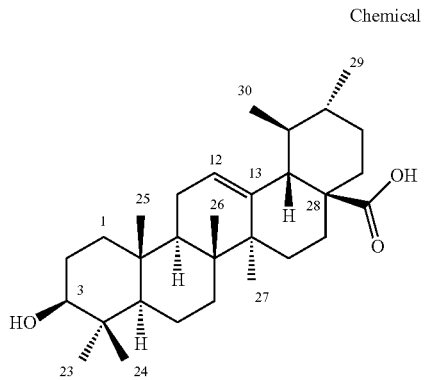

As shown in Chemical Formula 1 above, the ursolic acid has a basic structure of pentacyclic triterpene, and has a hydroxyl group at C-3 position, a double bond at C-12 position, and a carboxylic acid at C-28 position. It is known that the ursolic acid having the above-described structure is very poorly water-soluble, and is an optically active material having a significantly complicated structure including 10 chiral carbons.

Due to these characteristics, the ursolic acid is not possible to be chemically synthesized, and it is known that these materials are obtainable only by extraction and purification from the natural products such as plants, and the like, containing the ursolic acid in a large amount. However, since a content of the ursolic acid contained in the natural products such as plants, and the like, is not large, a significantly high cost is required to obtain the ursolic acid having high purity and high concentration by the extraction and the purification.

Meanwhile, the above-described ursolic acid is known as a functional cosmetic material. In particular, it has been reported that the ursolic acid is usable for skin improvement regarding photoaging and inflammation treatment. Meanwhile, the ursolic acid used as the functional cosmetic material generally has low purity and contains an oleanolic acid which is a structural isomer having hydrogen at C-29 position and dimethyl at C-30 position, and the like. Therefore, it is difficult to apply the low purity ursolic acid used as the cosmetic material as it is, for pharmaceutical usage.

Nevertheless, there are a number of reports that the ursolic acid is capable of being applied to various pharmaceutical products. For example, it has been reported that the ursolic acid inhibits NF-KB activation in living cells to enhance an efficacy of anti-cancer treatment-chemotherapy (see Int. J. Cancer (2010), 127, 462~473).

In addition, it has been reported that the ursolic acid exhibits excellent efficacy for treating and preventing muscle atrophy (see Cell Metabolism (2011) 13, 627~638). Besides, it has been reported that the ursolic acid is used in treatment of hepato fibrosis (see J of Hepatology (2011) 55, 379~387), and it has been known that the ursolic acid has a possibility of being used in treatment of hyperlipidemia by activating PPAR-α (see Bioorg Med Chem Lett (2011) 21, 5876~5880).

In addition, some research into an ursolic acid derivative capable of more enhancing efficacy of the ursolic acid or having new efficacy has been made.

For example, an ursolic acid derivative having phosphate at C-3 position is disclosed in EP1889850A1, and a derivative in an amine salt form obtained by combining a carboxylic acid at C-28 position of the ursolic acid with piperazine, and the like, is disclosed in U.S. Pat. No. 3,909,089. In addition, a derivative having a carboxy propionyloxy group at C-3 position of the ursolic acid and exhibiting activity as an anti-ulcer agent is disclosed in U.S. Pat. No. 4,530,934. Further, an ursolic acid derivative having an acyloxy group at C-3 position and a C5 to C8 alkyl group substituted for the carboxyl group at C-28 position is disclosed in US2011/0190388A1, wherein the ursolic acid derivative is usable as an anti-inflammatory agent and anti-cancer agent.

Even through the ursolic acid or derivatives thereof have various pharmacokinetic availabilities and efficacies as described above, research into formulation containing the ursolic acid has a limitation since the ursolic acid has poor water-solubility and extremely low oral absorptivity, for example, less than 1% and it is difficult to prepare a high purity ursolic acid.

SUMMARY OF INVENTION

Technical Problem

The present invention has been made in an effort to provide a novel ursolic acid derivative as an ursolic acid prodrug form, which can have excellent pharmacokinetic characteristics such as stability and oral absorptivity, and exhibit excellent pharmaceutical activities by being converted into an ursolic acid in vivo, and a method for preparing the same.

Solution to Problem

An exemplary embodiment of the present invention provides an ursolic acid derivative represented by Chemical Formula 2 below:

Chemical Formula 2

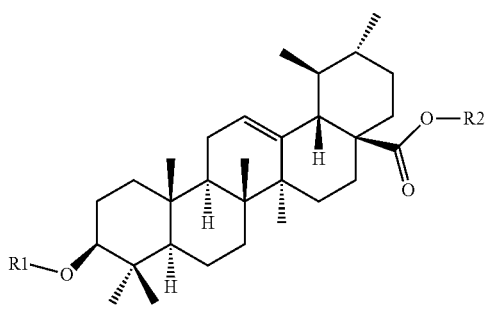

in Chemical Formula 2, $R_1$ is hydrogen or an acetyl group, and $R_2$ is

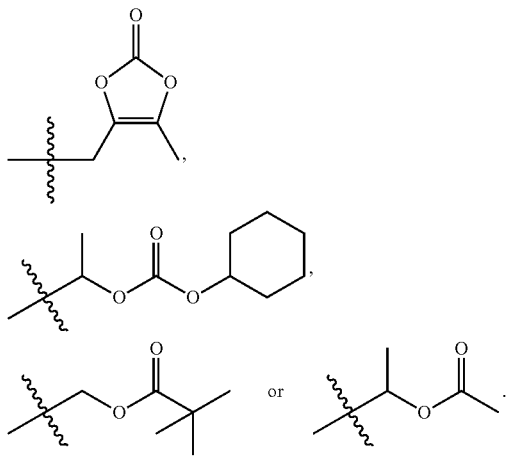

Chemical Formula 3

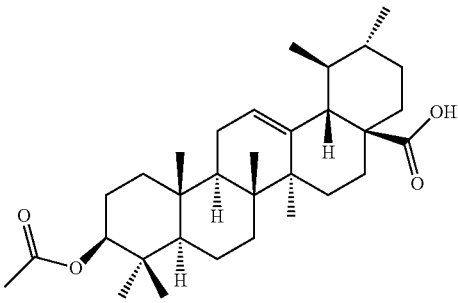

$R_2$—X    Chemical Formula 4 in Chemical Formula above, $R_2$ is

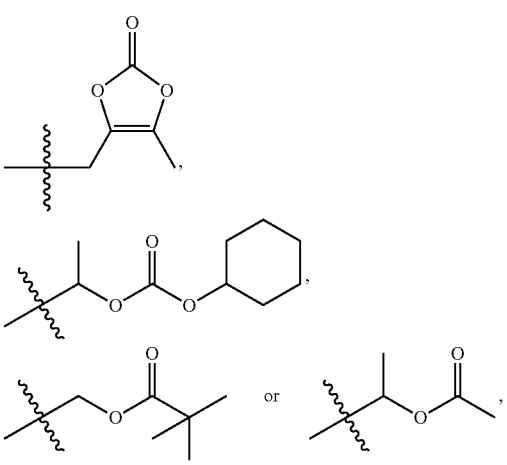

and

X is halogen radical of chloro (Cl), bromo (Br) or iodine (I).

Hereinafter, the ursolic acid derivative according to a specific exemplary embodiment of the present invention and the method for preparing the same will be described.

According to an exemplary embodiment of the present invention, there is provided the ursolic acid derivative represented by Chemical Formula 2. The ursolic acid derivative has an ester structure in which a predetermined functional group, $R_2$, is introduced into a carboxylic acid at C-28 position of the ursolic acid. Here, $R_2$ is a (5-methyl-2-oxo-1,3-dioxol-4-yl)methyl group derived from a prodrug of olmesartan (olmesartan medoxomil); a 1-[[(cyclohexyloxy)carbonyl]oxy]ethyl group derived from a prodrug of cefotiam (cefotiam hexetil); a [(2,2-dimethylpropanoyl)oxy]methyl group derived from a prodrug of valproate acid (valproate pivoxil); or a 1-[(4-methoxy-butanoyl)oxy]ethyl group derived from a prodrug of cefuroxime (cefuroxime axetil).

It is known that when the specific functional group, $R_2$, is introduced into a water-insoluble drug such as olmesartan, cefotiam, valproate acid, cefuroxime, or the like, oral absorptivity of the water-insoluble drug may be increased and stability in storage may be improved. However, examples in which the functional group, $R_2$, is introduced into the ursolic acid have not been known so far.

Another exemplary embodiment of the present invention provides a method for preparing the ursolic acid derivative as described above, including:

forming a compound represented by Chemical Formula 3 below by acetylation of an ursolic acid represented by Chemical Formula 1 below; and esterifying the compound represented by Chemical Formula 3 below with $R_2$—X represented by Chemical Formula 4:

Chemical Formula 1

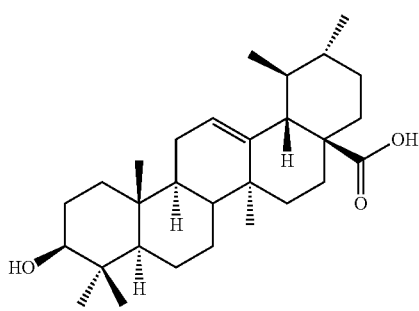

As the experimental results, the present inventors surprisingly found that in the urosolic acid derivative represented by Chemical Formula 2 above, which is the prodrug in the ester form, obtained by introducing the predetermined functional group, $R_2$, into the carboxylic acid at a specific position, that is, C-28 position of the ursolic acid, low oral absorptivity (for example, less than 1%) and formulation stability of the ursolic acid could be significantly improved. In addition, the functional group, $R_2$, may be rapidly metabolized and decomposed in vivo by specific enzymes, for example, a de-esterifying enzyme, and the like. As a result, the ursolic acid represented by Chemical Formula 2 is converted into the ursolic acid form in vivo, such that excellent unique pharmaceutical activities of the ursolic acid may be exhibited.

Therefore, the ursolic acid derivative represented by Chemical Formula 2 may solve problems such as low oral absorptivity, bioavailability, and the like, of the ursolic acid, and may exhibit excellent unique pharmaceutical activities in vivo, which may contribute largely to application of the ursolic acid or derivatives thereof to pharmaceutical formulation, by applying and introducing the known and commercially available esters in the prodrug form which are obtained from olmesartan, cefotiam, valproate acid, or cefuroxime, to the ursolic acid.

In addition, the ursolic acid derivative may be obtained by chemical synthesis to be described below from the ursolic acid. Therefore, it is easier to purify the ursolic acid so as to have a high purity, which may contribute largely to pharmaceutical and industrial utilization of the urosolid acid or the derivatives thereof.

Meanwhile, as described above, the ursolic acid derivatives represented by Chemical Formula 2 may have a structure in which the predetermined functional group, $R_2$, is introduced into the carboxylic acid at C-28 position, and optionally, may have a structure in which an acetyl group is introduced into the hydroxyl group at C-3 position. In the structure of the ursolic acid derivative, the functional group, $R_2$, may be rapidly decomposed by enzymes in vivo, and may be converted into the ursolic acid, to thereby exhibit excellent unique pharmaceutical activities of the ursolic acid.

For example, the ursolic acid derivative may be used as anti-cancer agent and an enhancer of the anti-cancer agent (in particular, an enhancer in chemotherapy for anti-cancer treatment), or in treatment or prevention of muscle atrophy, or in treatment of hepatic fibrosis or hyperlipidemia, like the ursolic acid.

The above-described ursolic acid derivative represented by Chemical Formula 2 may be prepared by forming a compound represented by Chemical Formula 3 above by acetylation of the ursolic acid represented by Chemical Formula 1 above; and esterifying the compound represented by Chemical Formula 3 above with $R_2$—X. In addition, the preparation method may further include: after the esterification, deacetylating an esterified product. The method for preparing the ursolic acid derivative may be shown by Reaction Scheme 1 below:

Reaction Scheme 1

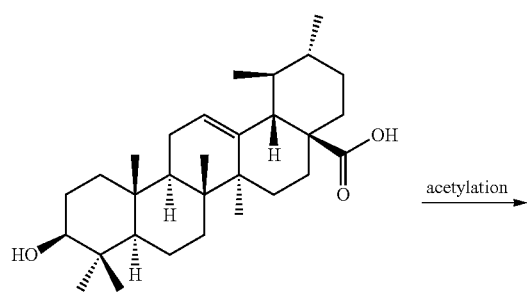

Chemical Formula 1: Ursolic Acid

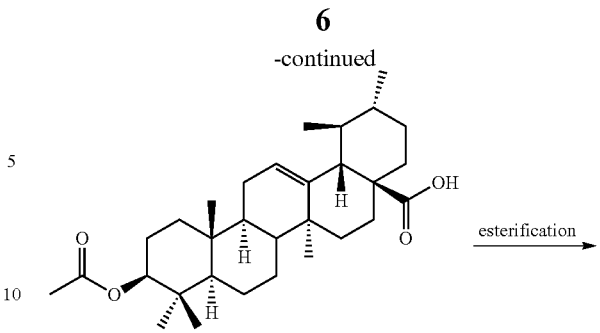

Chemical Formula 3

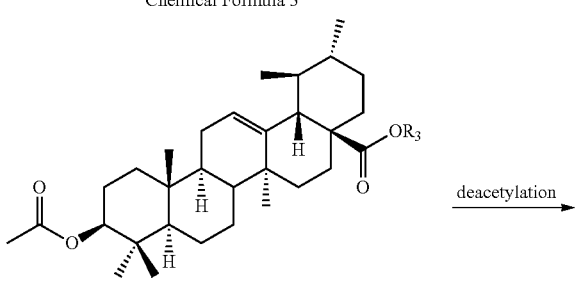

Chemical Formula 2 (R = Acetyl)

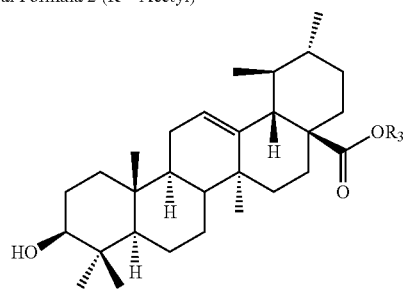

Chemical Formula 2 (R = Hydrogen)

Referring to Reaction Scheme 1 above, as a first acetylation step is processed in the preparation method, the acetyl group may be introduced into the hydroxyl group at C-3 position of the ursolic acid represented by Chemical Formula 1 to form the compound represented by Chemical Formula 3, and when the compound represented by Chemical Formula 3 is esterified with an electrophile compound of $R_2$—X, $R_2$ may be introduced into the carboxylic acid at C-28 position, thereby forming the ursolic acid prodrug in an ester form, that is, the ursolic acid derivative represented by Chemical Formula 2. Meanwhile, the thus-formed ursolic acid derivative has a structure in which the acetyl group is into the hydroxyl group at C-3 position (that is, $R_1$ in Chemical Formula 2 is the acetyl group), when an ursolic acid derivative represented by Chemical Formula 2 where $R_1$ is hydrogen is needed, a deacetylation step may be additionally processed.

The method for preparing the ursolic acid derivative as described above for each step is described as follows.

First, in first step, the ursolic acid represented by Chemical Formula 1 is acetylated to introduce the acetyl group into the hydroxyl group at C-3 position, thereby forming the compound represented by Chemical Formula 3. Here, the acetylation reaction may be performed in the presence of a base, for example, an amine base such as triethylamine, diisopropylethylamine, pyridine, or the like, and acetic anhydride, acetyl chloride, or the like, may be used as reaction materials for the acetylation. In some cases, the acetylation reaction may be performed in the presence of a catalyst such as N,N-dimethylaminopyridine.

In addition, in the acetylation reaction, a haloalkane-based solvent such as dichloromethane, a cyclic ether-based solvent such as tetrahydrofuran or dioxane, an ester-based solvent such as ethyl acetate, an amide-based solvent such as N,N-dimethylformamide a ketone-based solvent such as acetone, and the like, may be used as a reaction solvent, or a mixed solvent containing two or more selected therefrom may be used as the reaction solvent. Among them, the haloalkane-based solvent or the cyclic ether-based solvent may be appropriately used.

In addition, the acetylation reaction step may be performed at the reaction temperature at about 0° C. to 100° C., or about 10° C. to 30° C.

Then, in the second step, the compound represented by Chemical Formula 3 is esterified with the electrophile compound of $R_2$—X to introduce $R_2$ into the carboxylic acid at C-28 position, thereby forming the ursolic acid derivative represented by Chemical Formula 2 where $R_1$ is acetyl group. In the esterification reaction step, after the carboxylic acid at C-28 position is ionized, a nucleophilic substitution reaction may be performed by using the electrophile compound, thereby forming the ursolic acid derivative represented by Chemical Formula 2.

Therefore, the esterification reaction step may be performed in the presence of a base for ionizing the carboxylic acid at C-28 position, for example, an alkali metal base such as sodium hydroxide or sodium carbonate, or an alkaline earth metal base such as potassium hydroxide or potassium carbonate. Potassium carbonate may be preferably used.

In addition, specific examples of the electrophile compound of the $R_2$—X may include

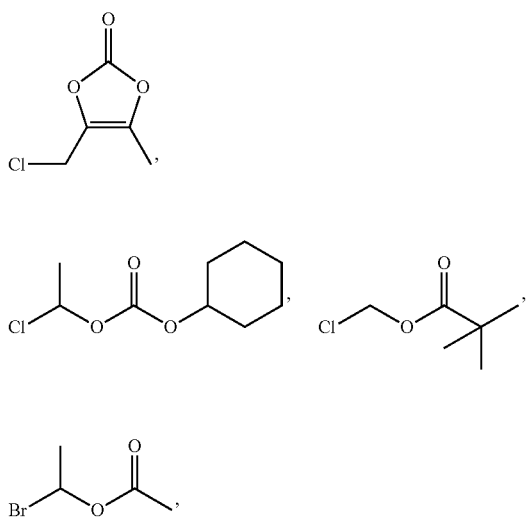

and the like, and by using the electrophile compound to perform the esterification reaction, the ursolic acid derivative represented by Chemical Formula 2 may be appropriately prepared. Specific examples of the electrophile compound may be referred to as a chemical name: 4-chloromethyl-5-methyl-2-oxo-1,3-dioxolene, 1-chloroethyl cyclohexyl carbonate, 1-chloromethyl pivalate or 1-(acetoxyethyl)bromide.

Among the electrophile compounds, 4-chloromethyl-5-methyl-2-oxo-1,3-dioxolene or 1-chloroethyl cyclohexyl carbonate is an optically active material having 10 chiral carbons, and an optical isomer thereof may be used, and preferably, racemate thereof may be used.

In addition, the electrophile compound may be used in about 1.0 to 3.0 equivalents, preferably, about 1.2 to 2.0 equivalents, and more preferably, about 1.4 to 1.6 equivalents, on the basis of the compound represented by Chemical Formula 3.

Further, in the esterification reaction step, a nitrile-based solvent such as acetonitrile, a ketone-based solvent such as acetone, or methylethylketone, an amide-based solvent such as N,N-dimethylformamide may be used as a reaction solvent, or a mixed solvent containing two or more selected therefrom may be used as the reaction solvent. Among them, the ketone-based solvent or the amide-based solvent may be appropriately used.

In addition, the esterification reaction step may be performed at a reaction temperature of about 0 to 100° C., or about 10 to 50° C.

In the above-described preparation method, the de-acetylation may be optionally performed as a third step, and therefore, the ursolic acid derivative in which $R_1$ is hydrogen may be prepared from the ursolic acid derivative represented by Chemical Formula 2 where $R_1$ is acetyl group.

In the deacetylation, the esterified product may be treated with acid or base in an alcohol solvent such as methanol, or the like. More specifically, the ursolic acid derivative may be deacetylated under basic conditions using a basic aqueous solution such as an aqueous solution of sodium hydroxide, an aqueous potassium carbonate, or ammonia water, in the alcohol solvent such as methanol, or the like. As other optionable method, the ursolic acid derivative may be deacetylated under acidic conditions using an acid such as 4-toluenesulfonic acid, or the like, or Lewis acid such as trifluoroborane diethyl ether, or the like, in the alcohol solvent.

Meanwhile, the deacetylation step may be performed under the above-described acidic conditions in the mixed solvent of the haloalkane-based solvent such as dichloromethane and the alcohol-based solvent such as methanol.

In addition, the deacetylation reaction step may be performed at a reaction temperature of about 0 to 100° C., or about 10 to 40° C.

Advantageous Effects of Invention

According to the present invention, there is provided a novel ursolic acid derivative, capable of significantly increasing low oral absorptivity and formulation stability of the ursolic acid, and being converted into an ursolic acid form in vivo to thereby exhibit excellent unique pharmaceutical activities.

Therefore, the ursolic acid derivative is possible to solve problems such as low oral absorptivity, bioavailability, and the like, of the ursolic acid, and to exhibit excellent unique pharmaceutical activities in vivo, which may contribute largely to application of the ursolic acid or derivatives thereof to pharmaceutical formulation.

DESCRIPTION OF EMBODIMENTS

Hereinafter, exemplary embodiments of the present invention will be described to assist in understanding the present invention. However, the following exemplary embodiments are provided only to more easily understand the present invention. The present invention is not limited thereto.

Reference Example 1

Preparation of 3β-acetoxy-urs-12-en-28-oic acid (Chemical Formula 3)

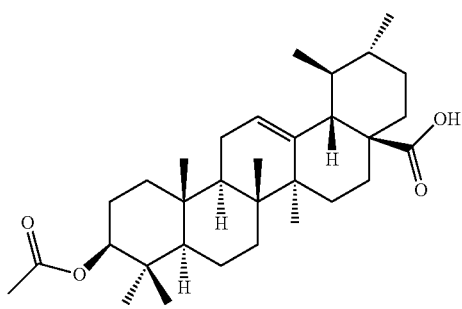

7.5 g of an ursolic acid (purity: 98%) was added to 50 ml of tetrahydrofuran at room temperature to be dissolved. Then, 6.45 g of pyridine and 0.2 g of N,N-dimethylaminopyridine were added thereto, followed by cooling to 10° C. or less, and 5.9 g of acetic anhydride was slowly added dropwise thereto. After the mixture was stirred at room temperature for 12 hours and the reaction completion was completed, the reaction liquid was concentrated. Here, the confirmation of the reaction completion was conducted by thin film chromatography (ethyl acetate: n-hexane=1:4 rf=0.4). The reaction concentrate was separated and purified by column chromatography using development solvent (ethyl acetate: n-hexane=1:2 to 2:1) to prepare 5.5 g of a target compound.

$^1$H-NMR (DMSO-d6, 500 MHz) 11.92 (1H. s), 5.12~5.14 (1H, t), 2.10~2.12 (1H, d, J=11.0 Hz), 2.00 (3H, s), 1.06 (3H, s), 0.91~0.92 (6H, d), 0.81~0.86 (9H, m), 0.76 (3H, s);

IR(cm$^{-1}$) 2924, 1734, 1686, 1459, 1367, 1245, 1027;

HPLC Purity: 99.0% or more (area ratio).

Example 1

Preparation of 5-methyl-2-oxo-1,3-dioxole-4-yl) methyl 3β-acetoxy-urs-12-en-28-oate

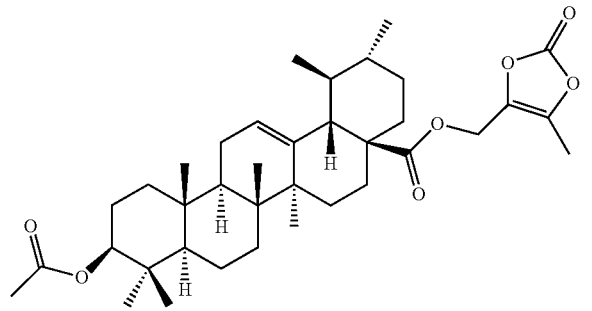

1.0 g of the compound obtained from Reference Example 1 was dissolved in 20 ml of acetone. 0.9 g of potassium carbonate and 0.4 g of potassium iodide (KI) were added thereto, and 0.6 g of 4-chloromethyl-5-methyl-2-oxo-1,3-dioxolane was added thereto. The mixture was reacted at room temperature for 24 hours and concentrated. 10 ml of ethyl acetate was added to the concentrate, the concentrate was washed with 10 ml of water and brine, respectively, and dried over anhydrous sodium sulfate. After filtration under reduced pressure and concentration to obtain residue, the residue was separated and purified by column chromatography to thereby obtain 0.7 g of a target compound.

$^1$H-NMR (DMSO-d6, 500 MHz) 4.76~4.99 (2H, dd) 5.17 (1H, t), 2.15~2.17 (1H, d, J=11.0 Hz), 2.11 (3H, s), 2.00 (3H, s), 1.06 (3H, s), 0.90~0.92 (6H, d), 0.81~0.86 (9H, m), 0.76 (3H, s);

IR(cm$^{-1}$) 2924, 1819, 1732, 1447, 1371, 1244, 1129, 1010.

Example 2

Preparation of 5-methyl-2-oxo-1,3-dioxole-4-yl) methyl 3β-hydroxyl-urs-12-en-28-oate

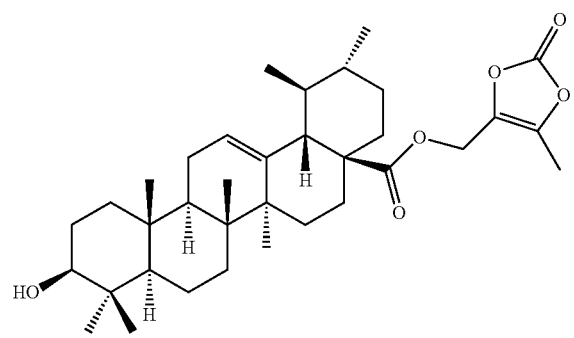

0.5 g of the compound obtained from Example 1 was dissolved in 4 ml of dichloromethane and 0.7 ml of methanol, and 0.68 g of 4-toluenesulfonic acid was added thereto, and the mixture was reacted al room temperature for 10 days. Then, 10 ml of dichloromethane and 10 ml oaf water were added thereto, extracted, and dried over anhydrous sodium sulfate, then filtrated. The obtained residue was separated and purified by column chromatography using development solvent (ethyl acetate: n-hexane=1:2 to 2:1) to prepare 0.3 g of a target compound.

$^1$H-NMR (DMSO-d6, 500 MHz) 4.76~4.99 (2H, dd) 5.16 (1H, t), 2.96~3.01 (1H, m), 2.14~2.16 (1H, d, J=11.5 Hz), 2.11 (3H, s), 1.04 (3H, s), 0.90~0.92 (3H, d), 0.88 (3H, s), 0.86 (3H, s), 0.81~0.86 (3H, d, J=11.5 Hz), 0.75 (3H, s), 0.56 (3H, s);

IR(cm$^{-1}$) 2918, 1822, 1686, 1720, 1455, 1383, 1219, 1186, 1044, 1029.

Example 3

1-[[(cyclohexyloxy)carbonyl]oxy]ethyl 3β-acetoxy-urs-12-en-28-oate

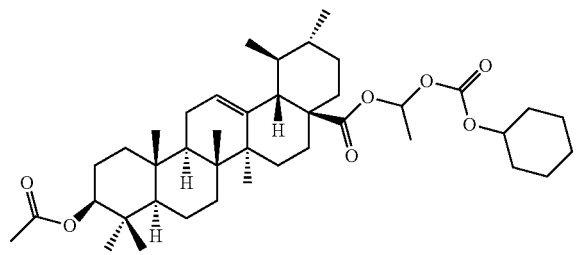

1.0 g of the compound obtained from Reference Example 1 was dissolved in 20 ml of acetone. 0.9 g of potassium carbonate and 0.4 g of potassium iodide (KI) were added thereto, and 0.65 g of 1-chloroethyl cyclohexyl carbonate was added thereto. The mixture was reacted at room temperature for 24 hours and concentrated. 10 ml of ethyl acetate was added to the concentrate, the concentrate was washed with 10 ml of water and brine, respectively, and dried over anhydrous sodium sulfate. After filtration under reduced pressure and concentration to obtain residue, the residue was separated and purified by column chromatography to thereby obtain 0.8 g of a target compound.

$^1$H-NMR (DMSO-d6, 500 MHz) 5.74~5.87 (1H, dd) 5.17 (1H, t), 3.0 (1H, m) 2.11~2.13 (1H, d, J=11.0 Hz), 2.00 (3H, s), 1.45 (3H, d), 1.06 (3H, s), 0.90~0.92 (6H, d), 0.81~0.86 (9H, m), 0.76 (3H, s), 1.00~2.20 (10H, m);

IR(cm$^{-1}$) 2925 1756 1732, 1697, 1466, 1373, 1245, 983.

Example 4

1-[[(cyclohexyloxy)carbonyl]oxy]ethyl 3β-hydroxyl-urs-12-en-28-oate

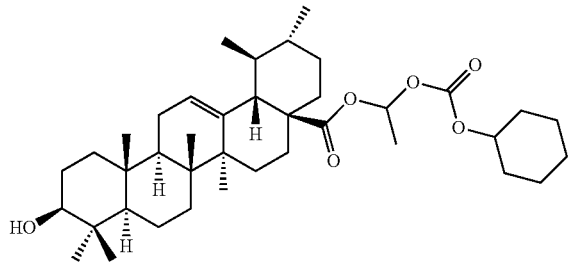

0.7 g of the compound obtained from Example 3 was dissolved in 4 ml of dichloromethane and 0.7 ml of methanol, and 0.68 g of 4-toluenesulfonic acid was added thereto, and the mixture was reacted at room temperature for 10 days. Then, 10 ml of dichloromethane and 10 ml of water were added thereto, extracted, and dried over anhydrous sodium sulfate, then filtrated. The obtained residue was separated and purified by column chromatography using development solvent (ethyl acetate: n-hexane=1:2 to 2:1) to prepare 0.4 g of a target compound.

$^1$H-NMR (DMSO-d6, 500 MHz) 5.70~5.85 (1H, dd) 5.17 (1H, t), 3.0 (1H, m) 2.11~2.13 (1H, d, J=11.0 Hz), 1.45 (3H, d), 1.06 (3H, s), 0.90~0.92 (3H, d), 0.88 (3H, s), 0.86 (3H, s), 0.81~0.86 (3H, d,), 0.75 (3H, s), 0.56 (3H, s), 1.00~2.20 (10H, m);

IR(cm$^1$) 2920, 1754, 1732, 1697, 1466, 1373, 1220.

Example 5

[(2,2-dimethyl-propanoil)oxy]methyl 3β-acetoxy-urs-12-en-28-oate

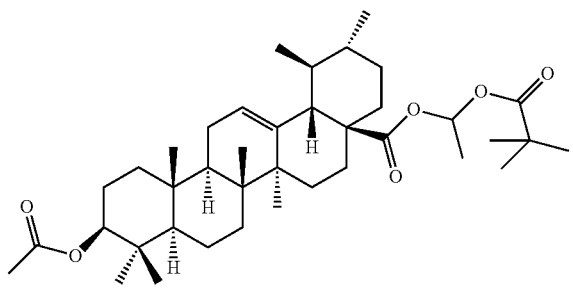

1.0 g of the compound obtained from Reference Example 1 was dissolved in 20 ml of acetone. 0.9 g of potassium carbonate and 0.4 g of potassium iodide (KI) were added thereto, and 0.55 g of 1-chloromethyl pivalate was added thereto. The mixture was reacted at room temperature for 24 hours and concentrated. 10 ml of ethyl acetate was added to the concentrate, the concentrate was washed with 10 ml of water and brine, respectively, and dried over anhydrous sodium sulfate. After filtration under reduced pressure and concentration to obtain residue, the residue was separated and purified by column chromatography to thereby obtain 0.7 g of a target compound.

$^1$H-NMR (DMSO-d6, 500 MHz) 5.63~5.68 (2H, dd) 5.16 (1H, t), 2.11~2.13 (1H, d, J=11.0 Hz), 2.02 (3H, s), 2.0 (3H, s), 1.13 (9H, m), 1.06 (3H, s), 0.90~0.92 (6H, d), 0.82 (9H, m), 0.71 (3H, s);

IR(cm$^1$) 2920, 1749, 1726, 1686, 1466, 1372, 1245, 1152.

Example 6

[(2,2-dimethyl-propanoil)oxy]methyl 3β-hydroxy-urs-12-en-28-oate

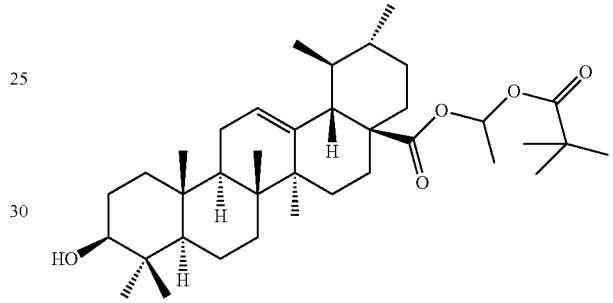

0.5 g of the compound obtained from Example 5 was dissolved in 4 ml of dichloromethane and 0.7 ml of methanol, and 0.68 g of 4-toluenesulfonic acid was added thereto, and the mixture was reacted at room temperature for 10 days. Then, 10 ml of dichloromethane and 10 ml of water were added thereto, extracted, and dried over anhydrous sodium sulfate, then filtrated. The obtained residue was separated and purified by column chromatography using development solvent (ethyl acetate: n-hexane=1:2 to 2:1) to prepare 0.3 g of a target compound.

$^1$H-NMR (DMSO-d6, 500 MHz) 5.63~5.68 (2H, dd) 5.17 (1H, t), 2.11~2.13 (1H, d, J=11.0 Hz), 3.0 (1H, m) 1.13 (9H, m), 1.04 (3H, s), 0.90~0.92 (3H, d), 0.88 (3H, s), 0.86 (3H, s), 0.81~0.86 (3H, d,), 0.75 (3H, s), 0.56 (3H, s);

IR(cm$^{-1}$) 2920, 1749, 1726, 1686, 1466, 1372, 1219, 1180.

Example 7

1-(acetoxy)ethyl 3β-acetoxy-urs-12-en-28-oate

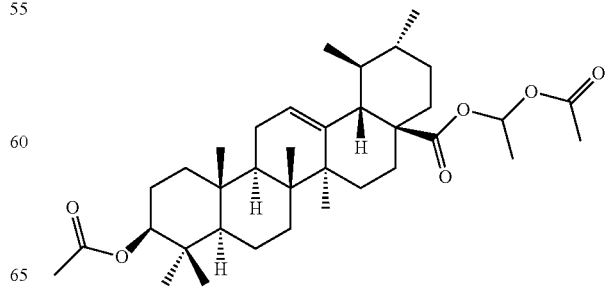

1.0 g of the compound obtained from Reference Example 1 was dissolved in 20 ml of acetone. 0.9 g of potassium carbonate was added thereto, and 0.6 g of 1-(acetoxyethyl) bromide was added thereto. The mixture was reacted at room temperature for 24 hours and concentrated. 10 ml of ethyl acetate was added to the concentrate, the concentrate was washed with 10 ml of water and brine, respectively, and dried over anhydrous sodium sulfate. After filtration under reduced pressure and concentration to obtain residue, the residue was separated and purified by column chromatography to thereby obtain 0.7 g of a target compound.

$^1$H-NMR (DMSO-d6, 500 MHz) 5.76~5.87 (1H, dd) 5.16 (1H, t), 2.11~2.13 (1H, d, J=11.0 Hz), 2.03 (3H, s), 2.0 (3H, s), 1.48 (3H, d), 1.13 (9H, m), 1.06 (3H, s), 0.90~0.92 (6H, d), 0.82 (9H, m), 0.71 (3H, s);

IR(cm$^{-1}$) 2920, 1750, 1728, 1690, 1465, 1370, 1245, 1152.

Example 8

1-(acetoxy)ethyl 3β-hydroxy-urs-12-en-28-oate

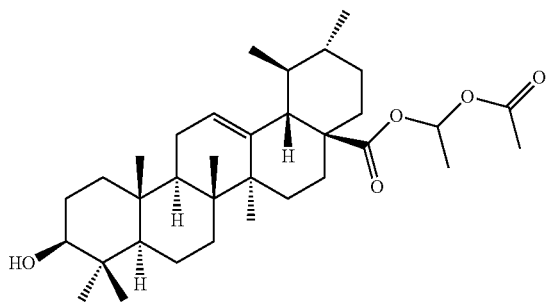

0.5 g of the compound obtained from Example 7 was dissolved in 4 ml of dichloromethane and 0.7 ml of methanol, and 0.68 g of 4-toluenesulfonic acid was added thereto, and the mixture was reacted at room temperature for 10 days. Then, 10 ml of dichloromethane and 10 ml of water were added thereto, extracted, and dried over anhydrous sodium sulfate, then filtrated. The obtained residue was separated and purified by column chromatography using development solvent (ethyl acetate: n-hexane=1:2 to 2:1) to prepare 0.3 g of a target compound.

$^1$H-NMR (DMSO-d6, 500 MHz) 5.75~5.85 (1H, dd) 5.16 (1H, t), 3.0 (1H, m), 2.11~2.13 (1H, d, J=11.0 Hz), 2.02 (3H, s), 1.45 (3H, d), 1.06 (3H, s), 0.90~0.92 (3H, d), 0.88 (3H, s), 0.86 (3H, s), 0.81~0.86 (3H, d,), 0.75 (3H, s), 0.56 (3H, s);

IR(cm$^{-1}$) 2925, 1752, 1730, 1695, 1464, 1370, 1220

Experimental Example

Pharmacokinetic Animal Test on Sprague Dawley (SD) Rat, Using Ursolic Acid and Ursolic Acid Derivatives of Examples Ursolic acid derivative of Examples (5-methyl-2-oxo-1,3-dioxole-4-yl)methyl 3β-hydroxyl-urs-12-en-28-oate was used.

A. Test Purpose

The ursolic acid was single-intravenously administered on SD rats and the ursolic acid derivative of Example 2 was orally administered, then blood collection was performed each time, and concentration of the test substance in blood was analyzed. Accordingly, bioavailability of the ursolic acid and ursolic acid derivatives of Examples were measured and compared with each other.

B. Control Substance and Test Substance i) Control substance (Intravenous Administration): Ursolic Acid (UA) (HPLC purity of 99.0% or more/area percentage)

ii) Test substance (Oral Administration) Ursolic acid derivative of Example 2 (HPLC purity of 99.4% or more/area percentage)

C. Preparation of Test Substance

The control substance for intravenous administration was diluted with 0.9% saline which was sterilized and sealed to be prepared in 0.5 mg/mL.

The test substance for oral administration was diluted with 0.9% saline which was the same as the test substance, to be prepared in 25 mg/mL, then diluted to be prepared in 12.5 mg/mL.

D. Test Materials and Method

[Test System]

(1) Species and strain: specific pathogen free (SPF) SD rats
(2) the number of used animals and gender: male 18
(3) Weight range: within about 180 g±20%
(4) Weight ranges when administration starts: within the average body weight (g)±20%
(5) Other details for animal test were followed with reference to the Food and Drug Administration Notice No. 2009~183 (Dec. 22, 2009), Good Laboratory Practice (GLP), and OECD Principles of Good Laboratory Practice (1997).

[Test Groups Configuration and Dose Setting]

(1) Test Groups Configuration:

Test groups configuration was shown in Table 1 below.

TABLE 1

| Group | Route of Administration | Number of Animals | Gender | Number | Dose (mg/kg) | Injection Amount (mL/kg) |
|---|---|---|---|---|---|---|
| G1 | Intravenous Administration | 6 | M | 1-6 | UA: 0.5 | 1 |
| G2 | Oral | 6 | M | 7-12 | Example 2: 25 | 2 |
| G3 | Oral | 6 | M | 13-18 | Example 2: 50 | 2 |

(2) Dose Setting

Dose setting was determined with reference to paper 1 below.

Paper 1: Dong Won Jeong, Hye Suk Lee et al., Dose-linear pharmacokinetics of Oleanolic acid after intravenous and oral administration in rats. Biopharm. Drug Dispos. (2007) 28:51-57.

[Administration and Blood Collection]

(1) Route of Administration: Route of administration was determined with reference to paper 1.

(2) Number of Administration and Duration of administration: Intravenous and single administration (3) Calculation of Injection Amount: The injection amount was calculated to be 1.0 or 2.0 mL/kg, on the basis of the recently measured body weight before the administration.

(4) Administration Method: For intravenous administration, an animal to be administered was put into a compensator, and tail was disinfected with 70% alcohol cotton, then the alcohol component was removed by using gauze, and the substance was administered by bolus using a 260 needle. For oral administration, the animal was fixed by a dorsocervical skin fixation method, and the substance was directly injected into the stomach using a sonde for oral administration.

(5) Blood Collection

Intravenous administration: After 0, 5, 15, 30, 45 minutes, and 1, 2, 4 and 8 hours (10 times) from the administration of test substance, 0.6 mL of whole blood was collected and stored in a tube treated with heparin (5 IU/mL) to separate blood plasma, and an overall amount was stored in one tube.

Oral administration: After 0, 5, 15, 30, 45 minutes, and 1, 2, 4, 8, and 12 hours (9 times) from the administration of test substance, 0.6 mL of whole blood was collected and stored in a tube treated with heparin (5 IU/mL) to separate blood plasma, and an overall amount was stored in one tube.

(6) Plasma Separation and Storage

After blood collection, the blood plasma was separated by centrifugation at 10,000 rpm for 5 minutes. The separated blood plasma was stored in a Deep freezer at −75±5° C. until it is sent to laboratory.

E. Analysis Method

1. Analysis Target

Concentration of ursolic acid in the blood plasma of the rats was measured.

2. Analysis Condition

Blood plasma samples which were pre-treated were analyzed under the following HPLC/MS/MS conditions shown in Table 2 below.

TABLE 2

| | |
|---|---|
| HPLC | Agilent 1200 series LC system |
| Detector | AB API4000 LC/MS |
| Column | Phenomenex Luna C18 column (50 mm × 2.0 mm, 3 μm) |
| Mobile Phase | 10 mM Ammonium acetate: methanol = 10: 90, v/v |
| Flow Rate | 0.3 mL/min |
| Injection Amount | 5 μL |
| MRM | Ursolic Acid (m/z 455.4 > 455.2) |
| | Hydrochlorothiazide (m/z 296.0.269.0) |

3. Construction of Calibration Curve

The ursolic acid standard was dissolved in methanol to have a concentration of 1 mg/mL, kept in a freezer, AND then, the solution was diluted with a frozen blank blood plasma to prepare blood plasma samples so that the blood plasma of the ursolic acid has concentrations of 2, 5, 10, 50, 100, 500, and 1000 ng/mL. 100 ng/mL of an internal standard substance and 50 μL of hydrochlorothiazide were added to 50 μL of respective standard plasmas and mixed. 500 μL of methyl-1-tert-butyl ether was added thereto, followed by vortexing for 10 mins, and centrifugation at 13000 rpm for 5 mins. 450 μL of an organic layer was moved to a clean polypropylene tube, and completely dried under nitrogen. 120 μL of mobile phase was added to the residue so as to be dissolved, and 5 μL was taken and injected into LC-MS/MS. An area ratio of a peak of the ursolic acid to a peak of the internal standard substance was calculated to construct a calibration curve.

4. Treatment of Blood Plasma Sample

The blood plasma samples obtained by collecting blood from the animal each time and storing the blood at −70° C. or less was allowed to stand at room temperature to be dissolved and shaken, then, 50 μL was taken and pre-treated by the same method as the construction of calibration curve, and injected into LC/MS/MS.

5. Calculation of Blood Concentration

The area ratio of the peak of the ursolic acid to the peak of the internal standard substance was calculated from the obtained chromatogram, and the concentration of the ursolic acid in the blood plasma was calculated from the previously constructed calibration curve.

F. Pharmacokinetic analysis program

BA Calc. Pharmacokinetic analysis was conducted by non-compartment analysis (best fit) using BA Calc. 2007 (KFDA), and $AUC_{last}$, $C_{max}$, $T_{max}$ and $t_{1/2}$ were calculated. $AUC_{last}$ and $C_{max}$ results were performed by bioequivalence analysis.

G. Test results: Bioavailability

Bioavailability data obtained from the measurement results according to the above-described methods were summarized and shown in Table 3 below.

TABLE 3

| | | | | Bioavailablity (%) | |
|---|---|---|---|---|---|
| Route of Administration | Dose | $AUC_{last}$ | $C_{max}$ | $AUC_{last}$ | $C_{max}$ |
| Intravenous Administration of Ursolic Acid | 0.5 | 114.33 | 378.50 | — | — |
| Oral Administration of Example 2 | 25 | 132.22 | 30.26 | 2.3 | 0.2 |
| | 50 | 127.05 | 29.20 | 1.1 | 0.1 |

Referring to Table 3, it was confirmed that as a result from the pharmacokinetic test on the rats using the ursolic acid derivative of Example 2, the ursolic acid derivative exhibited excellent oral absorptivity at dose of 25 mg/kg, and bioavailability of about 2.3%, which was increased about 3 to 4 times as compared to existing ursolic acid. Therefore, it is determined that the ursolic acid derivative is preferably applicable as an oral drug exhibiting excellent efficacy of the ursolic acid, unlike the ursolic acid which is not usable as an oral drug due to low oral absorptivity.

For reference, Paper 1 disclosed that as the pharmacokinetic test results on oleanolic acid which is an isomer having physicochemical characteristics which are similar to the ursolic acid, the oral absorptivity thereof was about 0.7%, and therefore, excellent oral absorptivity and bioavailability of the ursolic acid derivative of Example 2 could be also proven through the results of paper 1.

What is claimed is:

1. An ursolic acid derivative represented by Chemical Formula 2 below:

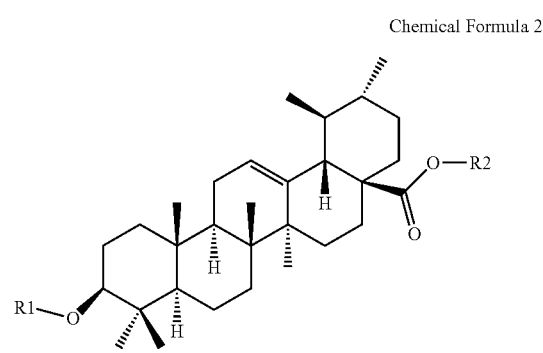

Chemical Formula 2 in Chemical Formula 2, $R_1$ is hydrogen or an acetyl group, and

R₂ is

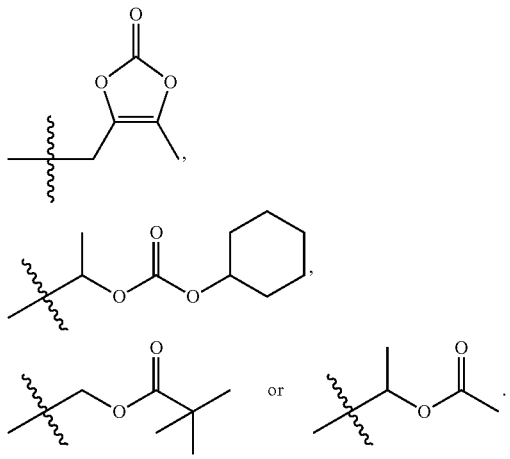

2. The ursolic acid derivative of claim 1, wherein the ursolic acid derivative is an ursolic acid prodrug which is converted into an ursolic acid in vivo.

3. A method for preparing the ursolic acid derivative of claim 1, comprising:
 forming a compound represented by Chemical Formula 3 below by acetylation of an ursolic acid represented by Chemical Formula 1 below; and
 esterifying the compound represented by Chemical Formula 3 below with R₂—X represented by Chemical Formula 4:

Chemical Formula 1

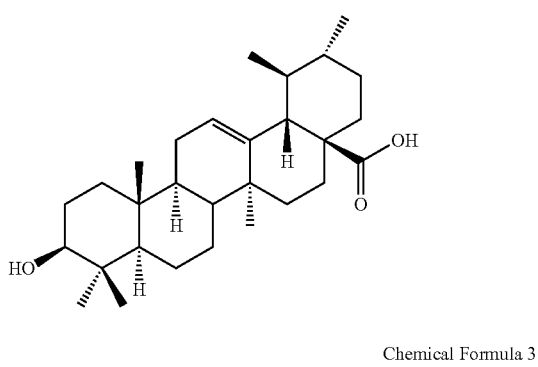

Chemical Formula 3

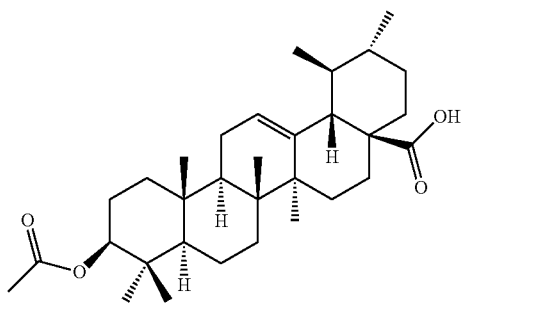

R₂+X    Chemical Formula 4 in Chemical Formula above,

R₂ is

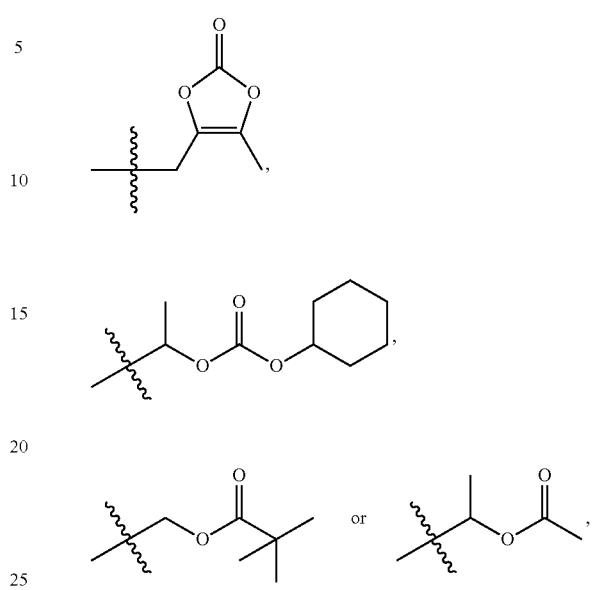

and

X is halogen radical of chloro (Cl), bromo (Br) or iodine (I).

4. The method of claim 3, further comprising a step of deacetylating an esterified product, after the esterifying.

5. The method of claim 3, wherein R₂—X represented by Chemical Formula 4 is

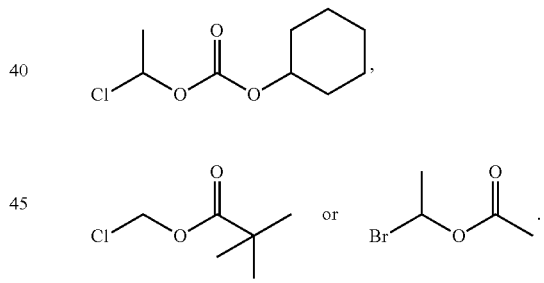

6. The method of claim 3, wherein in the acetylation, the ursolic acid represented by Chemical Formula 1 is reacted with acetic anhydride or acetyl chloride, in the presence of an amine base.

7. The method of claim 3, wherein in the esterifying, the compound represented by Chemical Formula 3 is reacted with R₂—X represented by Chemical Formula 4, in the presence of an alkaline metal base or an alkaline earth metal base.

8. The method of claim 4, wherein in the deacetylating, the esterified product is treated with acid or base in an alcohol solvent.

* * * * *